United States Patent [19]

Ross et al.

[11] Patent Number: 5,396,799

[45] Date of Patent: Mar. 14, 1995

[54] METHOD AND APPARATUS FOR IN SITU EVALUATION OF WOODEN MEMBERS

[75] Inventors: Robert J. Ross; Rodney C. De Groot, both of Madison; Earl A. Geske, Cross Plains; William J. Nelson, Madison; Vyto C. Malinauskas, Madison; Diego O. Cuevas, Madison, all of Wis.

[73] Assignee: The United States of America as represented by the Secretary of Agriculture, Washington, D.C.

[21] Appl. No.: 912,391

[22] Filed: Jul. 13, 1992

[51] Int. Cl.⁶ .................. G01H 1/00; G01N 29/04
[52] U.S. Cl. ........................ 73/579; 73/598; 73/600
[58] Field of Search ............ 73/579, 584, 587, 596, 73/597, 598, 599, 600

[56] References Cited

U.S. PATENT DOCUMENTS

| | | | |
|---|---|---|---|
| 2,549,076 | 4/1951 | Gallagher et al. | |
| 2,946,217 | 7/1960 | Fruengel | |
| 3,190,111 | 6/1965 | Trussel et al. | 73/579 |
| 3,209,177 | 9/1965 | Minasian | 73/579 |
| 3,345,861 | 10/1967 | Heath | |
| 3,521,483 | 7/1970 | Miller | |
| 3,531,983 | 10/1970 | Heath | |
| 3,580,056 | 5/1971 | Warner | 73/67.2 |
| 3,877,294 | 4/1975 | Shaw | 73/67.2 |
| 4,059,988 | 11/1977 | Shaw | 73/579 |
| 4,350,044 | 9/1982 | Richardson et al. | 73/600 |
| 4,399,701 | 8/1983 | Dunlop | 73/579 |
| 4,400,980 | 8/1983 | Lepert | 73/579 |
| 4,571,999 | 2/1986 | Arita et al. | 73/598 |
| 4,702,111 | 10/1987 | Holland | 73/579 |
| 4,858,469 | 8/1989 | Hosgood et al. | 73/579 |
| 4,918,988 | 4/1990 | Ebihara et al. | 73/594 |
| 4,926,691 | 5/1990 | Franklin et al. | 73/579 |

*Primary Examiner*—Richard E. Chilcot, Jr.
*Assistant Examiner*—William L. Oen
*Attorney, Agent, or Firm*—Janet I. Stockhausen; M. Howard Silverstein; John D. Fado

[57] ABSTRACT

A method for the non-destructive evaluation of the integrity of wooden members, in situ, for example, embedded in the soil, employing the reflection of an acoustic wave off of the embedded end of the wooden member. The reflection is caused by the discontinuity in acoustic properties between wood and the supporting medium. The method allows the measurement, at one end of the member, of substantially the entire length of the wooden member without its removal. The acoustic wave is monitored in time and amplitude to provide indications of sound speed and attenuation, measurements which apparently are not unduly affected by coupling losses between the wooden member and its supporting matrix. These measured values may be empirically linked in an equation providing the integrity of the wooden member.

11 Claims, 4 Drawing Sheets

METHOD AND APPARATUS FOR IN SITU EVALUATION OF WOODEN MEMBERS

BACKGROUND OF THE INVENTION

1. Field of the Invention

This invention relates to the nondestructive evaluation of a wooden member accessible from a single end, and having particular utility for evaluating wooden members having one end embedded in the soil, fresh or marine water, or the like, or otherwise inaccessible. It also has particular utility for test methods for monitoring biological or chemical degradation of wood products.

2. Background Art

Wooden members find a variety of applications in pilings for foundations, utility poles, and supports for guard rails. In these applications a portion of the wooden member is embedded in the soil to provide support for loads directed against the free end. Such wooden members provide an inexpensive but sturdy construction solution. For example, wooden pilings may carry 15 to 20 tons per piling.

Despite their strength and low costs, wooden members are subject to weakening from decay, insect infestation, and chemical attack. White and brown rot fungi may attack wood in contact with the soil, soft rot fungi and bacteria may attack woods maintained in even a low oxygen environment such as when submerged in fresh water. Wooden members embedded in the soil may also be attacked by subterranean termites, wood boring beetles, carpenter ants, and carpenter bees. Marine borers may attack wood used in marine waters. Chemicals, including those used to protect wood from biological attack or fire, may also weaken wooden members.

The destructive mechanisms of decay, and insect and chemical attack frequently cause internal damage or a weakening of the wood on a microscopic level not visible to the eye. Further, much of the damage may occur out of sight. For this reason, in most applications, it is critical that wooden members in contact with the soil or other medium, be inspected periodically to insure their integrity.

A variety of non-destructive tests are available to evaluate the integrity of a wooden member that is free from surrounding soil, water, other medium, or contact with other members. However, it is not practical to extract the wooden members for testing because of the disproportionate cost of such removal and reinsertion. Typically such wooden members are providing ongoing support for a structure, further complicating their removal.

Current testing procedures for wooden members in situ, that is embedded in the soil or other medium, are difficult and ineffective. Sample borings may be taken into the wooden member to evaluate its internal state if the area of possible damage may be localized. Alternatively, non-destructive x-ray and acoustic techniques may be employed to examine the internal structure of the wooden member. These latter techniques are effective only above the soil line, or a very small amount below the soil line, because of interference from the physical presence of the soil in which the wooden member is embedded and because both sides of the wooden member must be accessible.

SUMMARY OF THE INVENTION

The present invention provides a means for evaluating, from one end, the integrity of a wooden member, along the entire length of the wooden member. This includes those portions beneath soil line or otherwise not easily accessible. The need to have access to both ends of the wooden member is avoided by using an acoustic wave directed from the free end, longitudinally along the wooden member, so as to reflect off the embedded end of the wooden member, to be measured at the free end. The reflection occurs because of the discontinuity between the wooden member and its surrounding matrix.

Specifically, an acoustic wave is directed longitudinally from the first end of the wooden member to the second end embedded in a medium. A first time of passage of the acoustic wave toward the second end past a measurement point is detected as is a second time of the passage of the acoustic wave past the measurement point reflected from the second end toward the first end. The distance traveled by the acoustic wave between the first and second times is estimated and the longitudinal sound speed through the wooden member is calculated from the first and second times and the distance. This sound speed is compared to a reference speed to determine the integrity of the wood type.

Additionally, the attenuation of the acoustic wave over the reflected path may be evaluated, and the relationship between the sound speed and the attenuation may be evaluated by empirical studies to provide further indication of the strength of the wooden member.

It is thus one object of the invention to provide an accurate assessment of the wooden member's integrity throughout its entire length without removing the wooden member from the soil or other surrounding medium. The use of the reflected acoustic wave eliminates the need for a separate transmitter and receiver at opposite sides of the wooden member as required by typical acoustic evaluation techniques. Key to using this reflected wave was the discovery that the coupling of acoustic energy from the wooden member into its surrounding medium of soil or water does not materially affect the information contained in the acoustic wave concerning the integrity of the wooden member.

It is yet another object of the invention to provide a convenient apparatus for measuring the integrity of in situ wooden members that may be conveniently used in the field by a single individual. The ability to make acoustic measurements from a single end of the wooden member permits one transducer unit to be employed for both transmitting and receiving the acoustic wave. This single transducer unit may be placed on the wooden member to be measured by an individual without assistance and does not require laborious positioning required by separate transducers. The single transducer unit may be enclosed in a compact housing adding to the unit's reliability and ruggedness.

It is another object of the invention to provide a robust measurement of the physical characteristics of an in situ wooden member useful in detecting damage to the wooden member from a broad variety of agents: such as chemicals, decay fungi, and insects. For example, degradation due to termite infestation previously was undetectable by wave speed alone. Employing both attenuation and speed of sound measurements eliminates the shortcomings of either measurement alone. It is believed that the combined measurements also serve to correct for inaccuracy in the estimate of the wooden member's length required for the calculation of sound speed.

The transducer unit may employ an impacting means for generating the acoustic wave and the wave may be detected by a piezoelectric film held against the wooden member's end.

It is another object of the invention, therefore, to provide a simple means for generating and detecting the required acoustic signals. The mass and velocity of the impacting means may be regulated to create an acoustic wave of suitable characteristics without complex or expensive electronic circuitry. The piezoelectric film provides good coupling to the irregular surface of the wooden member and has a damped response that eliminates obscuring high frequency resonances, such as those that would be encountered with more conventional acoustic pickups.

Other objects and advantages besides those discussed above shall be apparent to those experienced in the art from the description of the preferred embodiment of the invention which follows. In the description, reference is made to the accompanying drawings, which form a part hereof, and which illustrate one example of the invention. Such example, however, is not exhaustive of the various alternative forms of the invention, and therefore reference is made to the claims which follow the description for determining the scope of the invention.

BRIEF DESCRIPTION OF THE DRAWINGS

FIGS. 6(a) and (b) are graphs of actual signals received by the transducer of FIG. 2 for normal and weakened wooden members respectively.

DETAILED DESCRIPTION OF THE PREFERRED EMBODIMENTS

Figure 1:
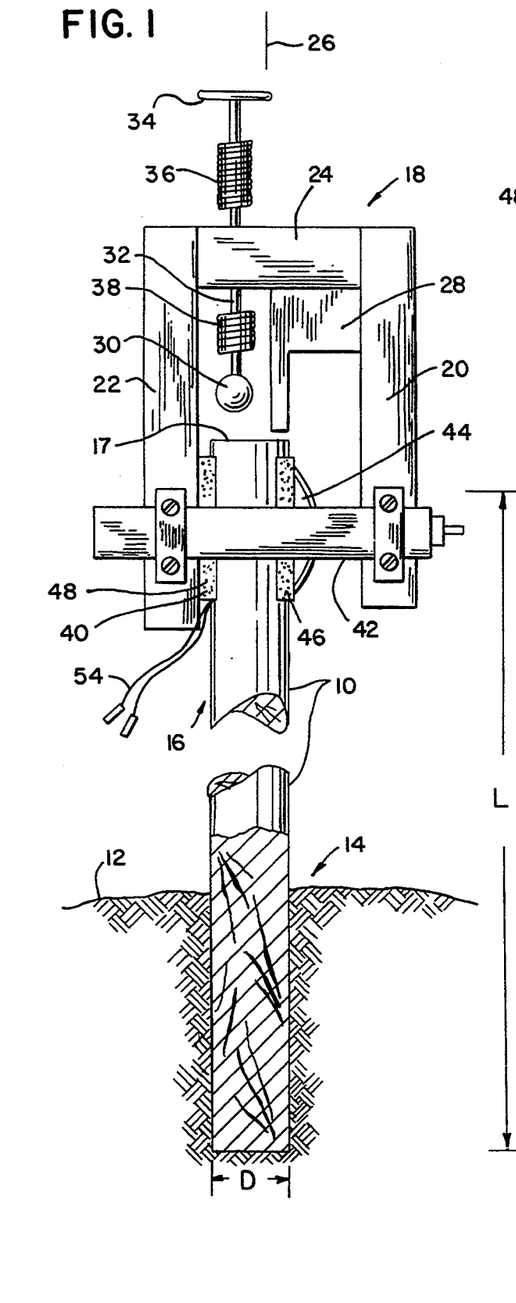
FIG. 1 is an elevational cross-section of a wooden member embedded in the soil having an apparatus suitable for use with the method of the present invention attached to the upper, exposed end.

Referring to FIG. 1, a wooden member 10, having diameter D extends vertically upward from the soil 12, centered around longitudinal axis 26. A lower end 14 of the wooden member 10 is embedded in the soil 12 such as would be the case with a piling or guard rail wooden member. An upper end 16 of the wooden member 10 projects out of the soil 12, to provide support for a structure (not shown) and is readily accessible for measurements as will be described.

A C-collar 18 having downwardly extending arms 20 and 22 spaced apart by spine 24 is positioned over the upper end 16 of the wooden member 10 so that arms 22 and 20 are diametrically opposed about the longitudinal axis 26 with the spine 24 positioned above an upper face 17 of the upper end 16 of the wooden member 10.

Spine 24 is spaced away from the upper face 17 of the wooden member 10 by a spacing finger 28 extending downward from the lower side of the spine 24 to abut the top of the upper face 17 when the C-collar 18 is properly positioned on the upper end 16.

The purpose of the spacing finger 28 is to create a space between the spine 24 of the collar 18 and the upper face 17 of the wooden member 10 sufficient for movement of an impacting means 30 between the lower surface of the spine 24 and the upper face 17 to strike the upper face 17 as will be described below. The impacting means 30 is a steel sphere suspended on a shaft 32 extending upward from the impacting means 30, parallel to the longitudinal axis 26, and passing through a hole in the spine 24 to emerge from the upper surface thereof. It will be understood to those of ordinary skill in the art that the impacting means 30 may have a variety of different shapes, preferably, however, it is shaped to concentrate its impact against upper face 17 about a point on the upper face 17. It will also be understood to those of ordinary skill in the art that the impacting means may be manufactured of substances other than steel, or that the impacting means could be mounted such that it strikes a location on wooden member 10 other than the upper face 17.

The shaft 32 above the spine 24 terminates in a T-handle 34 which may be employed to raise the shaft 32 and the impacting means 30 in preparation to its striking the upper face 17 of the wooden member 10.

A compression spring 36 is positioned about the shaft 32 between the upper surface of the spine 24 and the T-handle 34 and held by a pin (not shown) to the shaft 32 at its upper end. The spring 36 insures that after the impacting means 30 first strikes the upper face 17 it comes to rest at a position removed from the upper face 17 without repeatedly striking or resting on upper face 17.

A second spring 38 is positioned about shaft 32 between the lower face of spine 24 and the impacting means 30 to provide an initial acceleration of the impacting means 30 downward after it has been pulled up against the lower face of the spine 24 to fully compress spring 38. Spring 38 thus avoids the need to rely totally on the acceleration of gravity to generate the impacting means' momentum in striking the upper face 17.

Arm 22 of the C-collar 18 extends downward on one side of the upper end 16 of the wooden member 10, parallel to the longitudinal axis 26, to sandwich a transducer assembly 40 between it and the outer circumference of wooden member 10 at the upper end 16.

A spring loaded track 42 spans the gap between the lower end of arms 20 and 22, offset to the side of the upper end 16 of wooden member 10, and is clamped rigidly to the arms 20 and 22. A shoe 44, is carried by the spring loaded track 42 so as to oppose arm 22 diametrically about the wooden member 10. The spring loaded track 42 urges the shoe 44 inward toward the center of wooden member 10 sandwiching a foam pad 46 between the shoe 44 and the outer circumference of the wooden member 10. In urging the shoe 44 against the wooden member 10, the spring loaded track 42 exerts an opposite force on arms 20 and 22 thereby also serving to compress arm 22 against the outer circumference of wooden member 10 in an opposite direction to the force produced by the shoe 44 against the wooden member 10. Thus, the spring loaded track 42 and shoe 44 serve to clamp the upper end 16 of the wooden member 10 between arm 22 and shoe 44.

Figure 2:
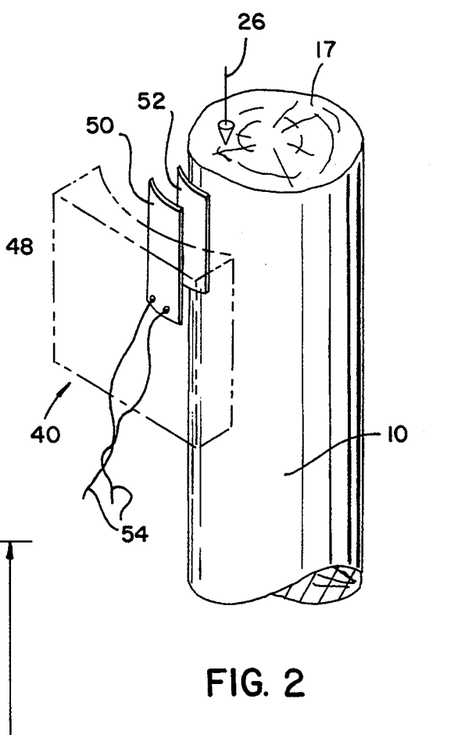
FIG. 2 is an exploded perspective view of a transducer employed in the apparatus of FIG. 1.

Referring now to FIG. 2, the transducer assembly 40 held by arm 22 against the wooden member 10 consists of a foam pad 48 substantially identical to foam pad 46, previously described, having an outer planar face affixed to arm 22 and an inner cylindrically concave face conforming to the outer circumference of the wooden member 10 at its upper end 16. Attached to the inner face of the foam pad 48, facing the wooden member 10, is a piezoelectric transducer 50.

Attached to the face of the piezoelectric transducer 50 toward the wooden member 10 is a sandpaper strip 52. Sandpaper strip 52 is a conventional paper-backed abrasive having on one side an adhesive to-attach it to the piezoelectric transducer 50 and having on the other side abrasive particles directed towards the outer circumference of wooden member 10. The abrasive particles provide a good mechanical coupling of the piezoelectric transducer 50 to longitudinal strain, i.e., strain parallel to the longitudinal axis 26 at the surface of wooden member 10, such strain being caused by deformation waves along longitudinal axis 26 produced by the impact of impacting means 30 against the upper face 17. The piezoelectric transducer 50 produces an electrical signal in response to the longitudinal deformation of wooden member 10 when the wooden member 10 is struck by impacting means 30, the electrical signal passing through wire pair 54 for connection to measuring circuitry to be described.

Referring to both FIG. 1 and FIG. 2, the only contact between the C-collar 18, via arm 22 and shoe 44, is through foam pads 46 and 48 which decouple the wooden member 10, acoustically, from the C-collar 18, with respect to high frequency vibration. The foam pad 48 serves additionally to compress the piezoelectric transducer 50 as attached to sandpaper strip 52 against the surface of wooden member 10, to couple it acoustically to the wooden member 10 and to decouple it acoustically from collar 18. Thus the foam pads 42 and 48 reduce interference to the acoustic waves in wooden member 10 from the C-collar 18.

The foam pads 48 and 46 are preferably constructed of an elastomeric foam such as polyurethane. The piezoelectric transducer 50 may be any conventional motion transducer, including accelerometers or strain gauges, but is preferably a piezoelectric organic film such as a polar poly-vinylidene fluoride film sold commercially under the name Kynar® piezoelectric film by the Pennwalt Corporation, of Valley Forge, Pa.

Figure 3:
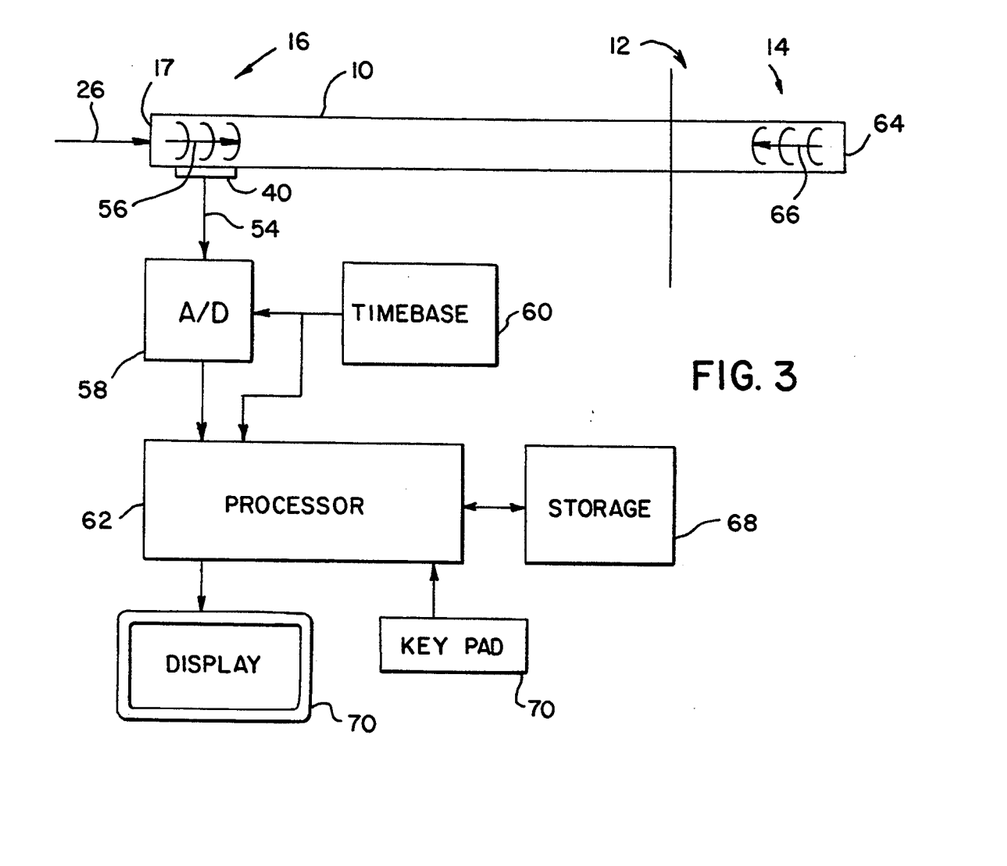
FIG. 3 is a diagrammatic view of a wooden member as evaluated by an apparatus according to the present invention showing the elements of the present invention in schematic form including the transducer of FIG. 2.

Referring now to FIG. 3, longitudinal deformation of the wooden member 10 creates an electrical signal in the transducer assembly 40 which passes through leads 54 to an analog digital converter 58 ("A to D converter"). The A to D converter 58 is triggered by a time base 60 to sample the signal created by the transducer assembly 40. A time value from the time base 60 and the digitized information reflecting the signal from the transducer assembly 40 from the A to D converter 58 are received by a processor unit 62 which may be a conventional microprocessor based computer.

During an initial measuring stage, the impacting means 30 (shown in FIG. 1) strikes the upper face 17 of the wooden member 10 to produce a primary acoustic wave 56 passing from the upper end 16 of the wooden member 10 toward the lower end 14. As this primary acoustic wave 56 passes the transducer assembly 40, the resultant deformation of the wooden member 10 under the transducer assembly 40 produces a signal sampled by the A to D converter 58 and stored by the processor 62. The processor 62 also stores corresponding time values from time base 60. This storage is accomplished in internal random access memory as will be understood by those of ordinary skill in the art.

The primary acoustic wave 56 produced by the impact of impacting means 30 against wooden member 10 progresses from the upper end 16 to the lower end 14 of the wooden member 10 passing into the portion of the wooden member 10 embedded in the soil 12. At the lower end 14, there is some coupling of acoustic energy from the primary wave 56 to the surrounding soil 12. It has been determined, however, that this coupling does not affect the acoustic measurements of the wooden member 10 to be described.

The primary acoustic wave 56 soon strikes the lower face 64 of the wooden member 10 at the lower end 14 and as a result of the mismatch of acoustic properties between the wooden member 10 and the soil 12, the primary acoustic wave 56 is reflected back onto itself to create a secondary acoustic wave 66 progressing from the lower end 14 of the wooden member 10 to its upper end 16.

When this secondary acoustic wave 66 passes the transducer assembly 40, its effect is again recorded by the A to D converter 58 and the digitized waveform is stored by processor 62 along with the times of the sampling as created by time base 60.

The storing of data from the transducer assembly 40 by processor 62 is triggered by the first detection of the signal of the primary acoustic wave 56 according to methods well understood in the art. The storing of data by processor 62 continues for a period of time sufficient to ensure capture of the secondary acoustic wave 66 for all wooden members 10.

Figure 4:
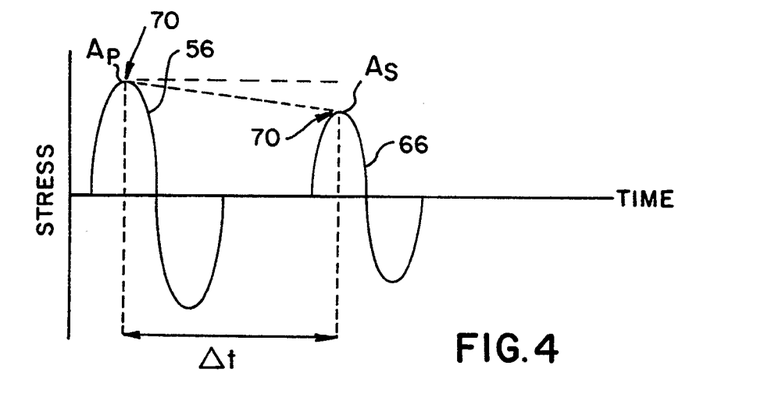
FIG. 4 is a graph showing simplified signals received by the transducer of FIG. 2 during a test of a wooden member.

Referring to FIG. 4, the primary acoustic wave 56 as recorded by the processor 62 will generally consist of a wave having a positive and negative going lobe reflecting the initial deformation of the elastic material of the wooden member 10, by impacting means 30, and its recovery in the opposite direction. The actual wave 56 will include multiple frequencies but will have dominant energies in a narrow band of frequencies dictated by the momentum of the impacting means 30 and the properties of the wood 10.

The momentum and energy of the impacting means 30 upon impact with upper face 17 is adjusted so that the predominant frequency of the waves 56 and 66 has a wave length which is long compared to D, the width of the wooden member 10. Under this constraint, the primary and secondary waves 56 and 66 will travel the length of the wooden member 10 with essentially constant velocity, $c_0$ as given by the follow formula:

$$c_0 = \sqrt{\frac{MOE}{\rho}} \quad (1)$$

where MOE is the modulus of elasticity or Young's modulus and $\rho$ is the density of the wood of wooden member 10.

Referring again to FIG. 3, once the primary and secondary acoustic waves 56 and 66 have been recorded by the processor 62, they may be transferred to storage unit 68 such as a floppy disk drive for later access. The processor 62 then analyzes the stored data to identify the peaks 70 of waves 56 and 66 and determines the time $\Delta t$ indicating the elapsed time between the passage of the primary wave 56 past the transducer assembly 40 and the return of the secondary acoustic wave 66 past the transducer assembly 40 as reflected off of the end 64 of the wooden member 10.

Based on an estimation of the length L between the end of the wooden member 64 and the center of the transducer assembly 40, the wave velocity $c_0$ through the wooden member 10, may be simply calculated as follows:

$$c_0 = \frac{2L}{\Delta t} \quad (2)$$

The value of L may be determined from records of the measurements of the wooden member 10 when first installed, and is entered through a keyboard 71 attached to the processor 62 as will be understood to those of ordinary skill in the art. As will be described in more detail below, the value of L need not be exact but the measurement process accommodates some variation in the estimate of L while still correctly evaluating the integrity of the wooden member 10. This is because the sound speed $c_0$ is significantly altered by certain types of damage to wooden member 10 so that only a reasonable estimate of L is required.

The processor 62 also compares the height of the peaks 70 of waves 56 and 66, respectively, to gauge the attenuation of the acoustic wave as it travels the length L through the wooden member 10. This attenuation is calculated from the peak amplitude of the primary acoustic wave 56, $A_p$ and the peak amplitude of the secondary acoustic wave 66, $A_s$ as follows:

$$\delta = \frac{1}{x} \ln\left(\frac{A_s}{A_p}\right) \quad (3)$$

where x is a normalizing value equal to either $\Delta t$ or L reflecting the fact that additional attenuation will occur as the wave goes through additional material of wooden member 10.

Referring again to FIG. 3, either of these quantities $c_0$ or $\Delta t$ may be displayed on a display 72, or similar output means, for direct evaluation by the user. Referring to equation (1), the modulus of elasticity, MOE, may also be calculated and displayed, provided the density $\rho$ of the wood has been previously entered through keyboard 71 into the processor 62.

EXAMPLE 1

An experiment was conducted employing 480 wooden members of various sizes ranging from 500 mm. to 1000 mm. The present invention was employed to measure the value of the modulus of elasticity, MOE, for the wooden members under three conditions: 1) with the wooden members completely removed from the soil, 2) with the wooden members buried approximately halfway into the soil, and 3) with the wooden members loosened from the soil by pulling them upward by approximately one inch. These latter two conditions provide variations in the degree of coupling between an embedded wooden member 10 and the soil 12.

Figure 5:
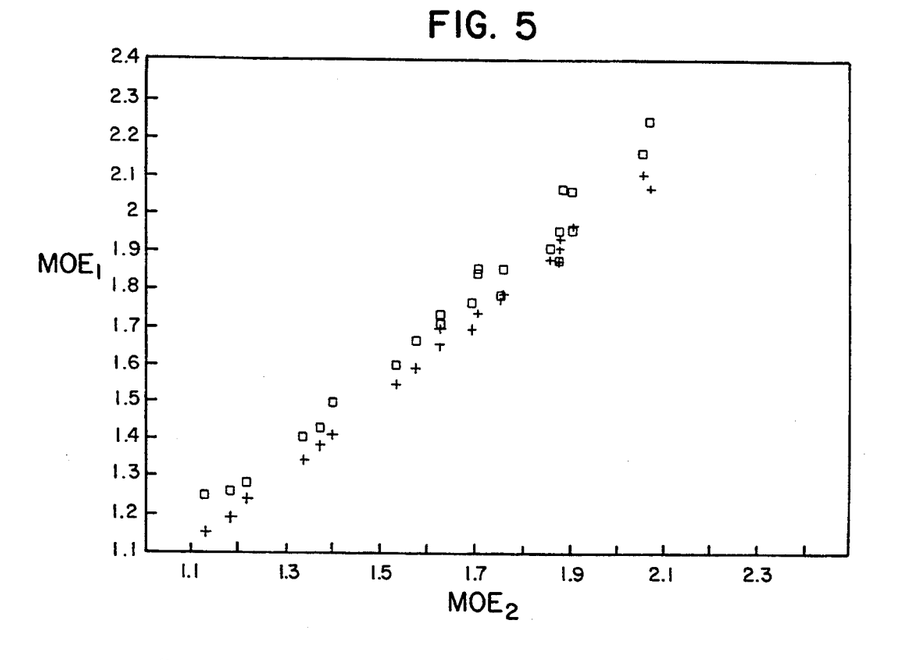
FIG. 5 is a chart showing correlation between the measurements achieved by the present invention on wooden members not embedded in the soil versus measurements achieved on wooden members touching or embedded in the soil.

Referring to FIG. 5, the measured modulus of elasticity for the wooden members embedded in the soil, $MOE_1$, were compared to the modulus of elasticity, $MOE_2$, of the wooden members removed from the soil. The modulus of elasticity of the wooden members embedded in the soil but prior to loosening is plotted as boxes in FIG. 5 and the modulus of elasticity of the wooden members embedded in the soil but loosened by raising them slightly is plotted as crosses in FIG. 5.

Despite unavoidable acoustic coupling between the wooden members and the soil, for the wooden members buried in the soil the value of $MOE_1$ and $MOE_2$, are similar for both the loosened and unloosened wooden members, indicating that the acoustic coupling between the soil and the wooden member 10 can be largely ignored.

Referring again to FIG. 3, preferably, processor 62 not only displays the various measured quantities of $c_0$, MOE, and $\delta$, but provides a direct evaluation of the integrity of the wooden member. This evaluation may be performed by establishing, through statistical techniques such as regression analysis, an equation linking the strength of the wooden member to the factors of modulus of elasticity, MOE, and attenuation, $\delta$, for a particular wood type. The coefficients of this equation, established, for example, through regression analysis, may be entered into the processor 62 and along with the measured values of MOE and $\delta$ provide a direct reading of wooden member strength or preferably a percentage value based on the strength of a new wooden member of comparable size.

It is believed that the redundancy in the measurement of MOE and $\delta$ provides a degree of correction to any inaccuracy in the estimate of L, the length of the wooden member 10, when the values of MOE and $\delta$ are combined through a regression derived formula as indicated above.

EXAMPLE 2

Figures 6A, 6B:
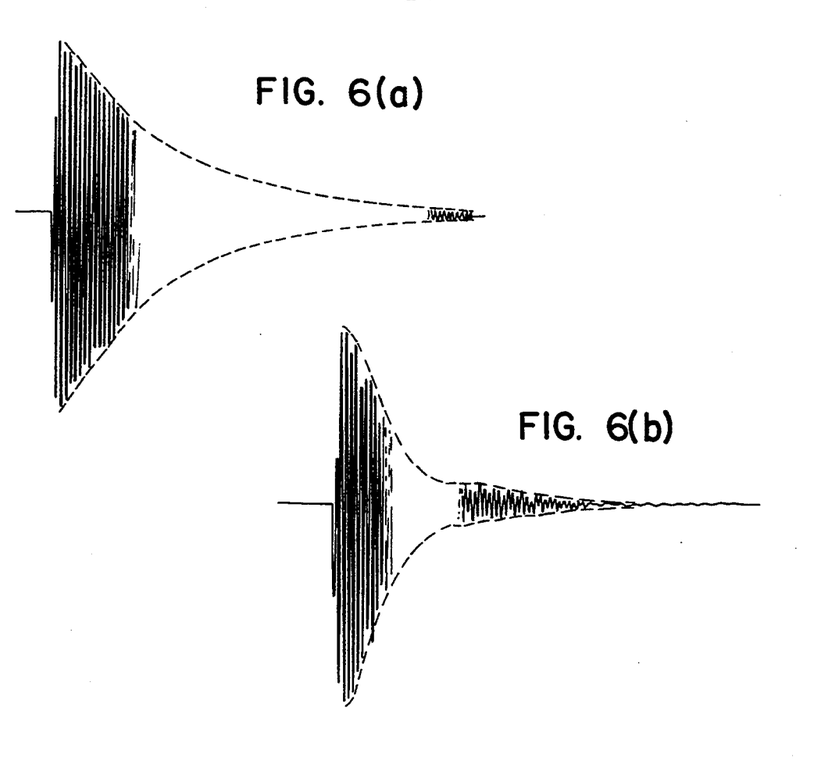

Two twenty inch wooden members of Southern Pine sapwood having one end embedded in the soil were tested: the first wooden member was free from decay or attack while the second wooden member had been attacked by subterranean termites during its two months of soil contact. FIGS. 6(a) and 6(b) show the waveforms from the acoustical excitation of the first and second wooden members respectively.

The length of the wooden members and the sound speed through the wood permit the measurement of the waves from repeated reflections off the embedded ends of the wooden members creating a clearly defined envelope showing the progressive attenuation of each wave. The difference in attenuation between attacked and unattacked wood is apparent.

EXAMPLE 3

Figure 7:
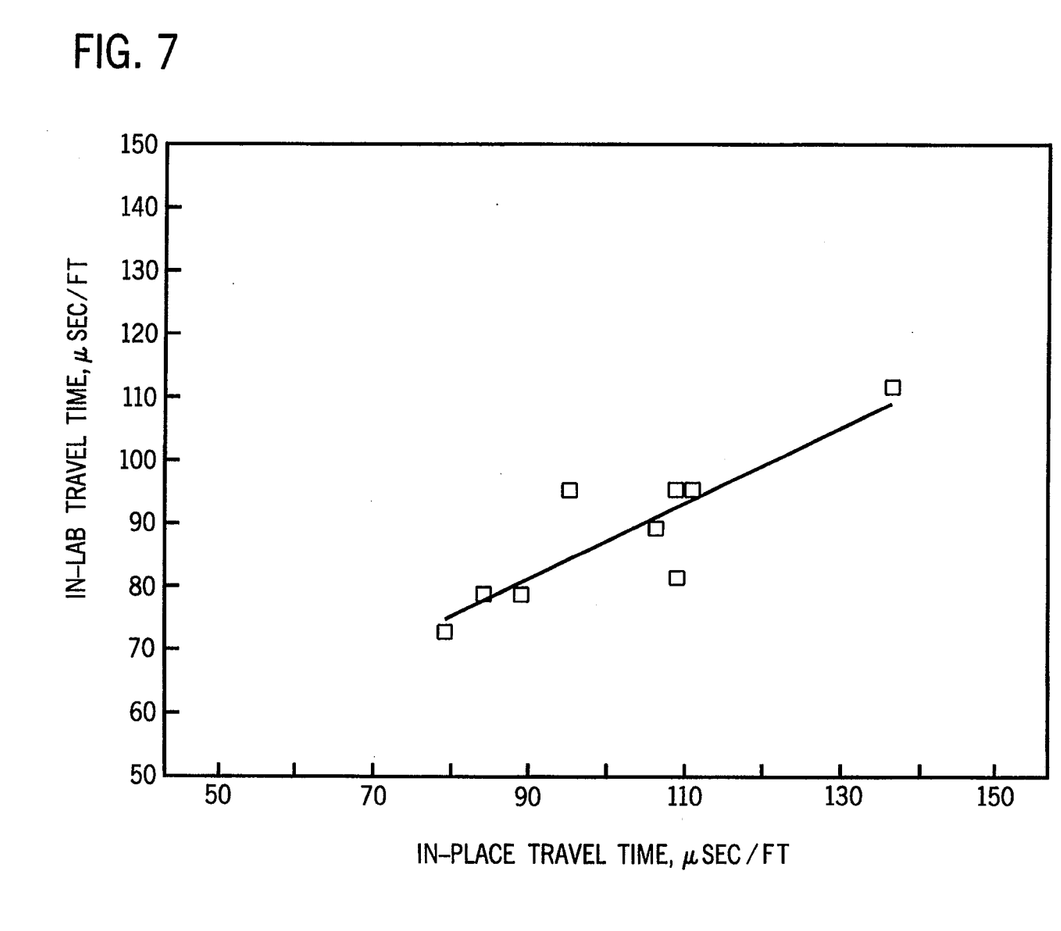
FIG. 7 is a chart showing correlation between the wave travel time in wooden members embedded in the soil versus the wave travel time in wooden members not embedded in the soil.

Nine wooden members of varying sizes were tested under two conditions: 1) with the wooden members buried approximately half-way into the soil, and 2) in the laboratory with the wooden members completely removed from the soil. FIG. 7 shows the wave travel times for both the first and second conditions.

The wave travel time through a wooden member will increase linearly as the length of the wooden member increases. FIG. 7 shows the in-ground and in-lab travel times plotted as boxes along such a linear increase. The similarity between wave travel times for the wooden members in-ground and in-lab is apparent from FIG. 7. This similarity indicates that the placing of wooden members into the soil or other mediums has no practical affect on the waves' travel time through the wooden members.

The above description has been that of a preferred embodiment of the present invention. It will occur to those who practice the art that many modifications may be made without departing from the spirit and scope of the invention. For example, although the wooden member depicted is substantially cylindrical, the technique is equally applicable to wooden members of other than circular cross section. Also, the wooden member need not have its upper face accessible but the acoustic wave may be coupled into the wooden member at any point at the upper exposed end, of known distance from the lower face. Such coupling may be accomplished by, for example, a collar affixed to the wooden member and having an outwardly extending boss to be struck by the impacting means. Also, clearly, other means of generating the acoustic wave may be used such as electrical transducers, if the additional burden of electronic circuitry is acceptable. Although, as shown, the transducer for receiving the wave is positioned between the wave generator and the reflecting lower face of the wave, the detecting transducer need not be so constrained in position as long as the transition time of the acoustic wave and its attenuation over a given path length may be deduced. In order to apprise the public of the various embodiment that may fall within the scope of the invention, the following claims are made.

We claim:

1. A method for testing the integrity of in situ wooden members of a wood type, the wooden members extending along a longitudinal axis from an exposed first end to a second end embedded in a medium, comprising the steps of:
    a) inducing an acoustic wave into the wooden member, the wave directed longitudinally from the first end to the second end;
    b) detecting a first time of a passage of the acoustic wave past a measurement point along the length of the wooden member during its travel to the second end;
    c) detecting a second time of a passage of the acoustic wave past the measurement point when reflected from the second end toward the first end;
    d) estimating the distance traveled by the acoustic wave between the first and second times;
    e) calculating the longitudinal sound speed through the wooden member from the first and second times and the distance;
    f) comparing the sound speed to a reference speed indicating integrity of the wood type; and
    g) outputting a value indicative of the integrity of the wooden member.

2. The method recited in claim 1 including the additional steps of:
    estimating the density of the wood type; and
    calculating the modulus of elasticity from the sound speed and density.

3. A method for testing the integrity of in situ wooden members of a wood type, the wooden members extending along a longitudinal axis from a first exposed end to a second end embedded in a conforming medium, comprising the steps of:
    a) coupling an acoustic wave into the wooden member, the wave directed longitudinally from the first end to the second end;
    b) detecting a first amplitude of the acoustic wave at a measurement point along the length of the wooden member during its passage toward the second end;
    c) detecting a second amplitude of the acoustic wave at the measurement point after being reflected from the second end toward the first end;
    d) calculating the sound attenuation through the wooden member from the first and second amplitudes; and
    e) comparing the sound attenuation to a reference attenuation indicating the integrity of the wood type.

4. The method recited in claim 3 including the steps of:
    estimating the distance between the measurement point and the second end of the wooden member;
    and wherein the calculated attenuation of step (d) is proportional to the difference of the first and second amplitudes and inversely proportional to the distance.

5. The method recited in claim 3 including the additional steps of:
    detecting at step (b) a first time when the first amplitude is detected and detecting at step (c) a second time when the second amplitude is detected:
    and wherein the calculated attenuation of step (d) is proportional to the difference of the first and second amplitudes and inversely proportional to the difference between the first and second times.

6. An apparatus for determining the integrity of in situ wooden members extending along a longitudinal axis from a first exposed end to a second end embedded in a medium, comprising:
    an excitation means attached to the wooden member near the first end and a length from the second end for generating in the wooden member a first acoustic wave, at a first time and of a first amplitude, directed longitudinally from the first end to the second end, and receiving a second acoustic wave, at a second time and of a second amplitude, the second acoustic wave resulting from the first acoustic wave being reflected from the second end of the wooden member;
    measurement means communicating with the excitation means for comparing the first and second acoustic waves and the length to indicate the integrity of the wooden member along its length between the excitation means and the second end;
    output means for outputting a value indicative of the integrity of the wooden member.

7. The apparatus as recited in claim 6 wherein the excitation means comprises:
    a wave generator for generating the first acoustic wave; and
    a wave detector for measuring the first acoustic wave as the first acoustic wave proceeds to the second end and the second acoustic wave as the second acoustic wave is reflected back to the excitation means and producing an electrical signal indicating the time and amplitude of the first and second acoustic waves.

8. The apparatus as recited in claim 6 wherein the measurement means compares the first and second times to evaluate the integrity of the wooden member.

9. The apparatus as recited in claim 6 wherein the measurement means compares the first and second amplitudes to evaluate the integrity of the wooden member.

10. The apparatus as recited in claim 7 wherein the wave detector means comprises a piezoelectric film attached to an outer circumference of the wooden member.

11. The apparatus as recited in claim 6 wherein the measurement means compares both the first and second times and the first and second amplitudes to evaluate the integrity of the wooden member.

* * * * *